United States Patent
Lee

(10) Patent No.: US 12,251,240 B2
(45) Date of Patent: Mar. 18, 2025

(54) METHOD FOR DISPLAYING BIOMETRICS INFORMATION

(71) Applicant: I-SENS, INC., Seoul (KR)

(72) Inventor: Jin Won Lee, Seoul (KR)

(73) Assignee: ISENS, INC., Seoul (KR)

( * ) Notice: Subject to any disclaimer, the term of this patent is extended or adjusted under 35 U.S.C. 154(b) by 846 days.

(21) Appl. No.: 17/430,674

(22) PCT Filed: Nov. 27, 2019

(86) PCT No.: PCT/KR2019/016459
§ 371 (c)(1),
(2) Date: Aug. 12, 2021

(87) PCT Pub. No.: WO2020/175767
PCT Pub. Date: Sep. 3, 2020

(65) Prior Publication Data
US 2022/0142589 A1 May 12, 2022

(30) Foreign Application Priority Data
Feb. 26, 2019 (KR) .................. 10-2019-0022426

(51) Int. Cl.
*A61B 5/00* (2006.01)
*A61B 5/145* (2006.01)

(52) U.S. Cl.
CPC ............ *A61B 5/743* (2013.01); *A61B 5/0004* (2013.01); *A61B 5/14532* (2013.01);
(Continued)

(58) Field of Classification Search
CPC ... A61B 5/743; A61B 5/0004; A61B 5/14532; A61B 5/6823; A61B 5/7275; A61B 5/7475; G09G 2380/08
See application file for complete search history.

(56) References Cited

U.S. PATENT DOCUMENTS

| 7,738,320 B2 | 6/2010 | Taha |
| 9,974,467 B2 | 5/2018 | Blahnik et al. |

(Continued)

FOREIGN PATENT DOCUMENTS

| JP | 60-148539 | 8/1985 |
| JP | 2006-99301 | 4/2006 |

(Continued)

OTHER PUBLICATIONS

International Preliminary Report on Patentability (Chapter I) for PCT/KR2019/016459 issued on Aug. 25, 2021 and its English translation from WIPO (now published as WO2020/175767).
(Continued)

*Primary Examiner* — Cao H Nguyen
(74) *Attorney, Agent, or Firm* — WOMBLE BOND DICKINSON (US) LLP

(57) ABSTRACT

The present disclosure relates to a method of displaying biological information. More specifically, the method allows sequential biological information to be easily displayed and checked using a small area by having the biological information sequentially displayed while rotating over a passage of time corresponding to measurement times of the biological information, and furthermore, by having biological information measured at a most recent measurement time displayed at a reference line, or by allowing biological information at a desired measurement time to be moved to the reference line by a clockwise or counterclockwise rotation, or by having measurement times displayed in a radial fashion in a single circle for each unit period so as to enable a user to select a desired unit period in a left direction or a right direction, the method allows for a user to easily change and check the biological information at the desired measurement time or unit period.

10 Claims, 10 Drawing Sheets

(52) U.S. Cl.
CPC .......... *A61B 5/6823* (2013.01); *A61B 5/7275* (2013.01); *A61B 5/7475* (2013.01)

(56) References Cited

U.S. PATENT DOCUMENTS

| | | | |
|---|---|---|---|
| 10,028,143 | B2 | 7/2018 | Lee et al. |
| 10,768,783 | B2 | 9/2020 | Lee et al. |
| 2008/0208027 | A1* | 8/2008 | Heaton .................. G16H 40/63 600/365 |
| 2009/0141593 | A1 | 6/2009 | Taha |
| 2012/0320079 | A1* | 12/2012 | Feddes .................. G06T 11/206 345/593 |
| 2019/0365243 | A1* | 12/2019 | Inoue .................... A61B 5/022 |

FOREIGN PATENT DOCUMENTS

| | | |
|---|---|---|
| JP | 2008-178669 | 8/2008 |
| JP | 2009-22671 | 2/2009 |
| JP | 2009-136677 | 6/2009 |
| JP | 2015-84861 | 5/2015 |
| JP | 2017-102654 | 6/2017 |
| JP | 2018-149175 | 9/2018 |
| KR | 2002-0018274 | 3/2002 |
| KR | 10-0408358 | 12/2003 |
| KR | 10-2014-0007184 | 1/2014 |
| KR | 10-2015-0054389 | 5/2015 |
| KR | 10-2016-0026497 | 3/2016 |
| KR | 10-2017-0003608 | 1/2017 |
| KR | 10-2017-0048779 | 5/2017 |
| WO | 2016/001800 | 1/2016 |
| WO | 2018/031803 | 2/2018 |

OTHER PUBLICATIONS

Office Action mailed on May 3, 2022 for Australian Patent Application No. 2019431856.
International Search Report for PCT/KR2019/016459 mailed on Mar. 9, 2020 and its English translation from WIPO (now published as WO 2020/175767).
Written Opinion of the International Searching Authority for PCT/KR2019/016459 mailed on Mar. 9, 2020 and its English translation by Google Translate (now published as WO 2020/175767).
Office Action mailed on Aug. 9, 2022 for Japanese Patent Application No. 2021-549533 and its English translation from Global Dossier.
Examination Report No. 1 dated Mar. 7, 2023 for New Zealand Patent Application No. 778991.
Notice of Allowance dated Apr. 15, 2021 for Korean Patent Application No. 10-2019-0022426 and its English translation from Global Dossier.
Office Action dated Sep. 24, 2020 for Korean Patent Application No. 10-2019-0022426 and its English translation from Global Dossier.
Extended European Search Report dated Sep. 13, 2022 for European Patent Application No. 19917418.6.
Office Action dated Apr. 5, 2023 for Japanese Patent Application No. 2021-549533 and its English translation from Global Dossier.
Office Action dated Dec. 7, 2022 for Japanese Patent Application No. 2021-549533 and its English translation from Global Dossier.

* cited by examiner (a)

(b)

(a)

(b)

METHOD FOR DISPLAYING BIOMETRICS INFORMATION

CROSS-REFERENCE TO RELATED APPLICATIONS

The present application is the U.S. National Phase of PCT Application No. PCT/KR2019/016459 filed on Nov. 27, 2019, which claims the priority to Korean Patent Application No. 10-2019-0022426 filed on Feb. 26, 2019, the entire contents of which are incorporated herein by reference.

TECHNICAL FIELD

Some exemplary embodiments of the present disclosure relate to a method for displaying biometrics information, more specifically, sequentially displaying biometrics information by rotating the biometrics information according to time flow of measurement times of the biometrics information so that sequential biometrics information can be easily displayed on a small display area, and locating biometrics information of most recently measured time at a reference line or moving biometrics information of a desired measurement time to a reference line by rotating in a clockwise or counterclockwise direction or displaying a measurement time by a unit period on a single circle in a radial form and selecting a unit period that a user desires by rotating in a left direction or a right direction such that the biometrics information of the desired measurement time or unit period can be easily changed and checked.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Blood glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

A continuous glucose monitoring system includes a sensor module attached to the skin of the human body and measuring a blood glucose level by extracting body fluid, a transmitter transmitting the blood glucose level measured by the sensor module to a terminal, and a user terminal outputting the received blood glucose level, and any other appropriate component so that the user can continuously monitor the blood glucose states of the user using blood glucose values periodically measured at several minutes.

In case of the blood-collecting type glucose monitoring system or the continuous glucose monitoring system, the measured blood glucose of the user is transmitted to a user terminal connected through wireless or wired communication, the user can check past or current blood glucose information of the user through the user terminal, and the type of displaying the blood glucose information through the user terminal displays only the blood glucose information measured at a specific time, or displays the blood glucose information measured according to sequential time with a table, or displays the blood glucose information measured according to time along an axis with a graph.

However, if only blood glucose information of a specific time is displayed, it is difficult to intuitively recognize changes to sequential blood glucose information, and if blood glucose information is represented by a table or graph, it is difficult to easily recognize changes to blood glucose information according to time flow.

Korean Patent Registration No. 10-0408358, entitled "Method of Displaying Biometrics Signal Data", published on Mar. 8, 2002 was published as conventional art of the present disclosure.

SUMMARY

Technical Problem

Certain embodiments of the present disclosure solve the above-mentioned problems of the conventional method of displaying the biometrics information, and the purposes of some embodiments of the present disclosure are for providing a method of rotating biometrics information according to time flow of measurement times of the biometric information and sequentially displaying the biometrics information.

Another purpose of certain embodiments of the present disclosure is for displaying biometrics information of latest measured time at a reference line or moving biometrics information of desired measurement time to the reference line by rotating in a clockwise or counterclockwise direction and displaying the biometrics information of the measurement time located at the reference line as an Arabic numeral so that the desired measurement time can be easily changed and the biometrics information can be precisely checked.

Still another purpose of certain embodiments of the present disclosure is for providing a method for displaying biometric information which is capable of displaying the biometrics information by unit periods, and easily changing to biometrics information of a unit period that a user desires by moving a left direction or a right direction and checking it.

Still another purpose of certain embodiments of the present disclosure is for providing a method for displaying biometric information which is capable of rotating and sequentially displaying biometrics information according to time flow of measurement times of the biometrics information so that the sequential biometrics information can be easily displayed on a small display area and checked.

Solution to Problem

For accomplish the purpose of the present disclosure, according to an embodiment of the present disclosure, a method for displaying biometrics information may comprise receiving biometrics information of a user; and sequentially displaying the received biometrics information on a display unit by rotating the received biometrics information around a reference level according to time flow of measurement times of measuring the biometrics information.

According to an embodiment of the method for displaying the biometrics information, the method for displaying the biometrics information locates latest measured biometrics information among the measurement times of measuring the biometrics information at a reference line, and sequentially displays previously measured biometric information by rotating the previously measured biometric information in a clockwise or counterclockwise direction from the reference line according to the time flow of the measurement times.

Preferably, the method for displaying the biometrics information according to an embodiment of the present disclosure further comprises: receiving a first user command for selecting measurement time which the user inquires to monitor among the biometric information received and rotated in the clockwise or counterclockwise direction; and rotately moving and displaying the received biometric information with reference to the reference line which is set by the measurement time, which the user inquires to monitor, selected according to the received first user command.

According to an embodiment of the method for displaying the biometrics information, the reference line is fixed and the received biometrics information is rotately moved with reference to the reference line which is the measurement time selected according to the first user command.

According to an embodiment of the method for displaying the biometrics information, when the first user command is not inputted within a preset threshold time, the latest measured biometrics information among the measurement times of measuring the biometrics information is located at the reference line and the previously measured biometric information is sequentially displayed by rotating the previously measured biometric information in the clockwise or counterclockwise direction from the reference line according to the time flow of the measurement times.

According to an embodiment of the method for displaying the biometrics information, the biometrics information measured at a measurement time located at the reference line is displayed with an Arabic numeral at one portion of the display unit.

Preferably, according to an embodiment of the method for displaying the biometrics information, the biometrics information measured at a measurement time located at the reference line is displayed with an Arabic numeral at a center of rotation.

Preferably, the method for displaying the biometrics information according to an embodiment of the present disclosure further comprises: receiving a second user information for setting a set value; and display the set value in a circular shape.

According to an embodiment of the method for displaying the biometrics information, biometrics information which is out of the set value among the received biometrics information is displayed with a different color from biometrics information which is within the set value.

Preferably, the method for displaying the biometrics information according to an embodiment of the present disclosure further comprises: determining whether biometrics information measured for a unit period is received; if the biometrics information measured for the unit period is received, mapping the received biometrics information to the unit period and registering and storing the received biometrics information mapped to the unit period; and rotating biometrics information received for a new unit period around the reference level according to the time flow of the measurement times of the biometrics information and sequentially display the biometrics information.

Preferably, the method for displaying the biometrics information according to an embodiment of the present disclosure further comprises: receiving a third user command for selecting the biometrics information of the unit period by moving in a left direction or a right direction; and displaying the biometrics information of the unit period which the user inquires to monitor by moving in the left direction or the right direction according to the received third user command.

According to an embodiment of the method for displaying the biometrics information, when the third user command is not inputted for a preset threshold time, biometrics information of a current unit period is displayed on the display unit.

Advantageous Effects of Invention

A method for displaying biometrics information according to various embodiments of the present disclosure may have following technical effects.

Firstly, a method for displaying biometrics information according to an embodiment of the present disclosure can easily display and check sequential biometrics information even in a small area by rotating and sequentially displaying inputted biometrics information according to time flow of measurement times of measuring the biometrics information.

Secondly, a method for displaying biometrics information according to an embodiment of the present disclosure can easily change desired measurement time and check biometrics information by displaying biometrics information of the most recently measured time at a reference line or moving biometrics information of desired measurement time to a reference line and displaying biometrics information of the measurement time located at the reference line with an Arabic numeral by rotating in a clockwise or counterclockwise direction.

Thirdly, a method for displaying biometrics information according to an embodiment of the present disclosure can easily change a unit period and check biometrics information by unit periods by displaying biometrics information in a single circle by unit periods and selecting a unit period desired by a user by moving in a left direction or right direction.

DETAILED DESCRIPTION OF EMBODIMENTS

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Additionally, singular expressions used in the present disclosure include plural meaning unless the context clearly dictates otherwise. In the present disclosure, the terms "comprising", "having", "including" and the like should not be construed to necessarily include all component elements or steps described in the present disclosure, and it should be interpreted that some component elements or some steps among them may not be included, or other components or steps may be added thereto.

Also, it should be noted that the accompanying drawings are merely illustrated to easily explain the spirit of the invention, and therefore, they should not be construed to limit the spirit of the invention by the accompanying drawings.

Figure 1:
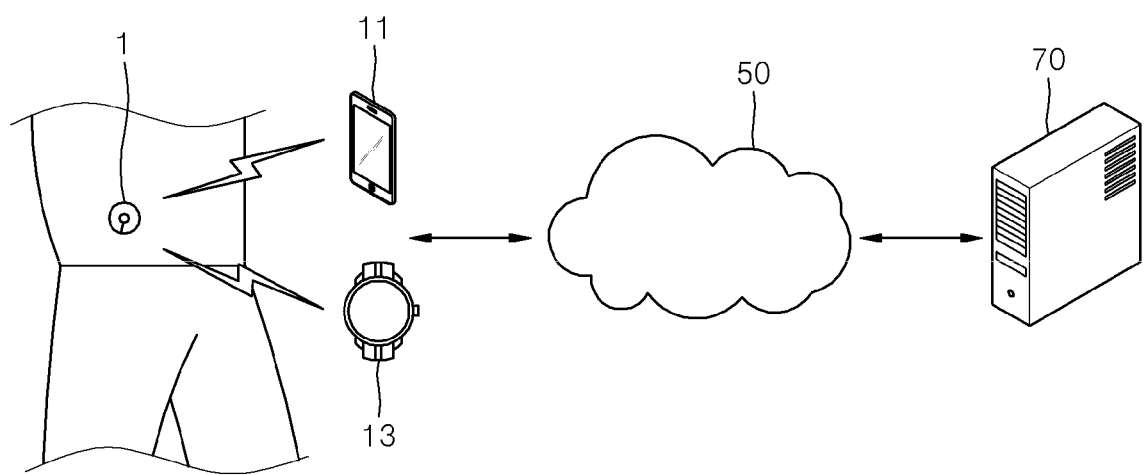
FIG. 1 is a drawing for illustrating a continuous blood glucose measurement system according to an embodiment of the present disclosure.

FIG. 1 is a drawing for illustrating a continuous blood glucose measurement system according to an embodiment of the present disclosure.

Referring to FIG. 1, a continuous blood glucose measurement device (1) is attached to a skin of a user, and the continuous blood glucose measurement device (1) periodically extracts the body fluid of the user and continuously measures biometrics information of the user (for example, blood glucose) using the extracted body fluid.

The continuous blood glucose measurement device (1) and user terminals (11, 13) are connected with each other through short-distance communication, such as Bluetooth communication, NFC communication (Near Field Communication), and so on, and the continuous blood glucose measurement device (1) and the user terminals (11, 13) receive and transmit data through the short-distance communication. Accordingly, when both the continuous blood glucose measurement device (1) and the user terminals (11, 13) are positioned within the short-distance communication range, the continuous blood glucose measurement device (1) transmits the measured biometrics information of the user to the user terminals (11, 13). Examples of the biometrics information measured by the continuous blood glucose measurement device (1) are described below.

More specifically, the user terminals (11, 13) may be a smartphone (11) or smart watch (13), when the smartphone (11) or the smart watch (13) is located within a certain distance from the continuous blood glucose measurement device (1), the smartphone (11) or the smart watch (13) initiates the connection process with the continuous blood glucose measurement device (1), and when the connection is completed, the smartphone (11) or the smart watch (13) periodically receives information of blood glucose measured by the continuous blood glucose measurement device (1).

The smartphone (11) or the smart watch (13) displays the most recent received blood glucose information among the glucose information received by the smartphone (11) or the smart watch (13) or sequentially outputs the blood glucose information continuously received for a certain time period according to time flow, and therefore the user can monitor a current blood glucose information of the user or can monitor the changes to the blood glucose information for a certain time period through a display unit of the smartphone (11) or the smart watch (13).

In this embodiment, the user terminal may be a device configured to store or output the blood glucose information of the user received from the continuous blood glucose measurement device (1) to the user so that the user can check the blood glucose information of the user received from the continuous blood glucose measurement device (1), and an application provided for this purpose of managing blood glucose information can be executed at the user terminal.

The user terminal (11, 13) is connected with a management server (50) through a network (30). The user terminal (11, 13) is configured to transmit the blood glucose information of the user received from the continuous blood glucose measurement device (1) to the management server (50) or transmits sensor use information of the continuous blood glucose measurement device (1) to the management server (50).

Preferably, the user terminal (11, 13) identifies a user based on inputted user information, and performs mapping between the blood glucose information and the identified user and registers and stores the blood glucose information mapped to the identified user. Meanwhile, the user terminal (11, 13) transmits the blood glucose information or the sensor use information registered and mapped to the user together with the user information to the management server (50).

Figure 2:
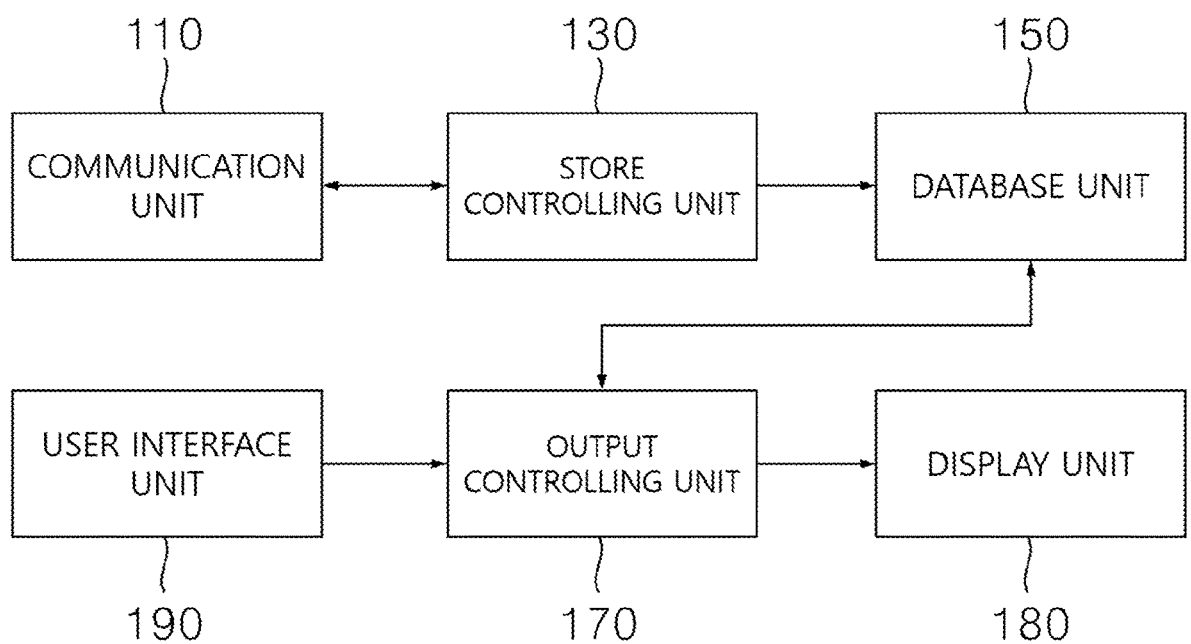
FIG. 2 is a functional block diagram for illustrating a user terminal for inquiring blood glucose information of a user according to an embodiment of the present disclosure.

FIG. 2 is a functional block diagram for illustrating a user terminal for inquiring blood glucose information of a user according to an embodiment of the present disclosure.

Referring to FIG. 2, a communication unit is communicationally connected with a continuous blood glucose measurement device and transmits/receives data to/from the continuous blood glucose measurement device when the communication unit (110) is located within a certain communication distance from the continuous blood glucose measurement device, and the communication unit (110) may be implemented as a short-distance communication unit for transmitting/receiving data to/from the continuous blood glucose measurement device, for example, a Bluetooth communication unit, NFC communication unit, infrared communication unit, and so on.

When a store controlling unit (130) receives the blood glucose information of the user from the continuous blood glucose measurement device through the communication unit (110), the store controlling unit (130) registers and stores the received blood glucose information to a database unit (150).

Meanwhile, an output controlling unit (170) controls operation of outputting the blood glucose information of the user registered and stored in the database unit (150) on a display unit (180), and the output controlling unit (170) controls to sequentially display the blood glucose information registered and stored in the database unit (150) on the display unit (180) by rotating the blood glucose information registered and stored in the database unit (150) around a reference blood glucose level according to time flow of measurement times of measuring the blood glucose. Specifically, the output controlling unit (170) controls to sequentially display and rotate the blood glucose information, which has been received from the continuous blood glucose measurement device and stored for a unit period (for example, a day, a week and so on), in a clockwise or counterclockwise direction according to time flow of the measurement times of measuring the blood glucose information on the display unit, and the latest measured blood glucose information among the received blood glucose information is located on a reference line and previously measured blood glucose information is controlled to be sequentially displayed by being rotated in a clockwise or counterclockwise direction according to the time flow of the measurement times from the reference line.

A user interface unit (190) is configured to receive a user command, and the user can input the user command for setting a set value of an upper limit blood glucose or a set value of a lower limit blood glucose through the user interface unit (190), or can input the user command for inquiring, checking or searching biometrics information to be outputted on the display unit (180). The output controlling unit (170) controls to display the set value of the upper limit blood glucose or the set value of the lower limit blood glucose together with the blood glucose information on the display unit (180) based on the set value of the upper limit blood glucose or the set value of the lower limit blood glucose, or controls to display the biometrics information by rotating the biometrics information so that specific measurement time that the user intends to inquire, check or search is located on the reference line or controls to display the biometrics information by moving to the unit period of the biometrics information that the user intends to inquire, check or search according to the user command for inquiring, checking or searching the biometrics information.

Figure 3:
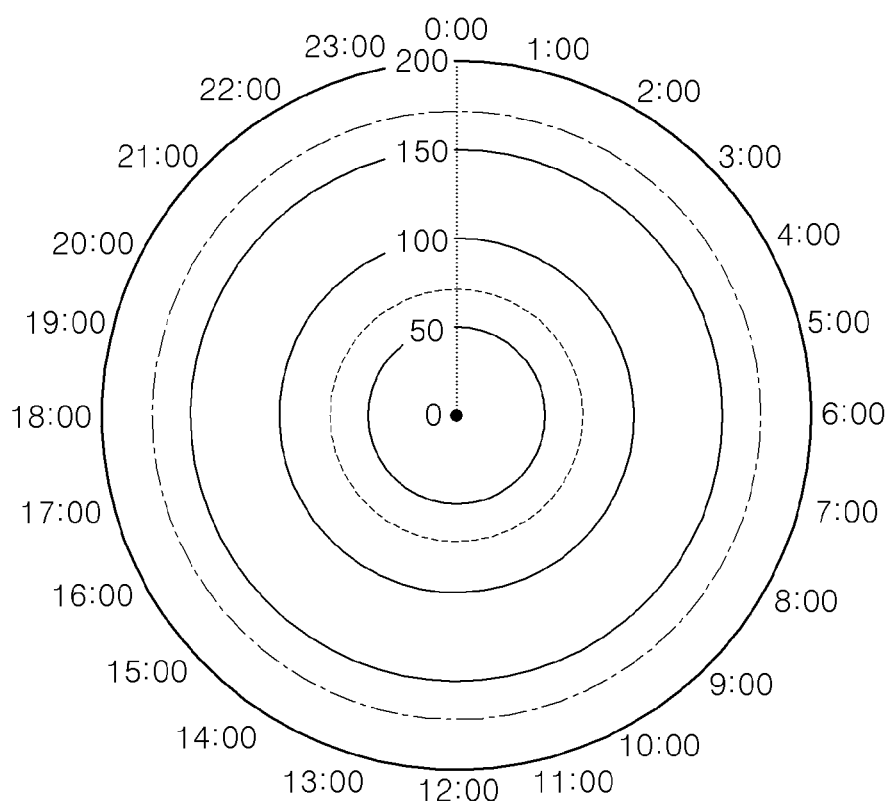
FIG. 3 illustrates an exemplary embodiment of blood glucose information displayed on a display unit.

FIG. 3 illustrates an exemplary embodiment of blood glucose information displayed on a display unit.

Referring to FIG. 3, circles representing sequentially increasing or decreasing blood glucose level around a reference blood glucose level, which may be a center of a circle, is displayed in a radial form or shape, and measurement times are displayed around the outermost circle. When the unit period displaying the blood glucose information on a single display screen is one day, measurement times for 24 hours are displayed around the outermost circle at regular intervals.

Meanwhile, when a set value of an upper limit blood glucose or a set value of a lower limit blood glucose is inputted through a user interface unit, a circle representing the set value of the upper limit blood glucose or the set value of the lower limit blood glucose at a blood glucose level corresponding to the set value of the upper limit blood glucose or the set value of the lower limit blood glucose is displayed. Preferably, the circle representing the set value of the upper limit blood glucose or the set value of the lower limit blood glucose is displayed with a different color from a circle representing a blood glucose level (for example, red or blue).

Accordingly, circles representing blood glucose levels which are sequentially increased or decreased from a reference blood glucose level, which may be a center of a circle, are displayed, and a blood glucose value and a measurement time of the measured blood glucose information are mapped to the blood glucose levels and time of a unit period and are displayed to be sequentially rotatedly moved in a clockwise direction or a counterclockwise direction, and therefore biometrics information of the user is displayed according to sequential time flow so that the user can easily recognize the biometrics information of the user on the display unit with a small size.

Figure 4:
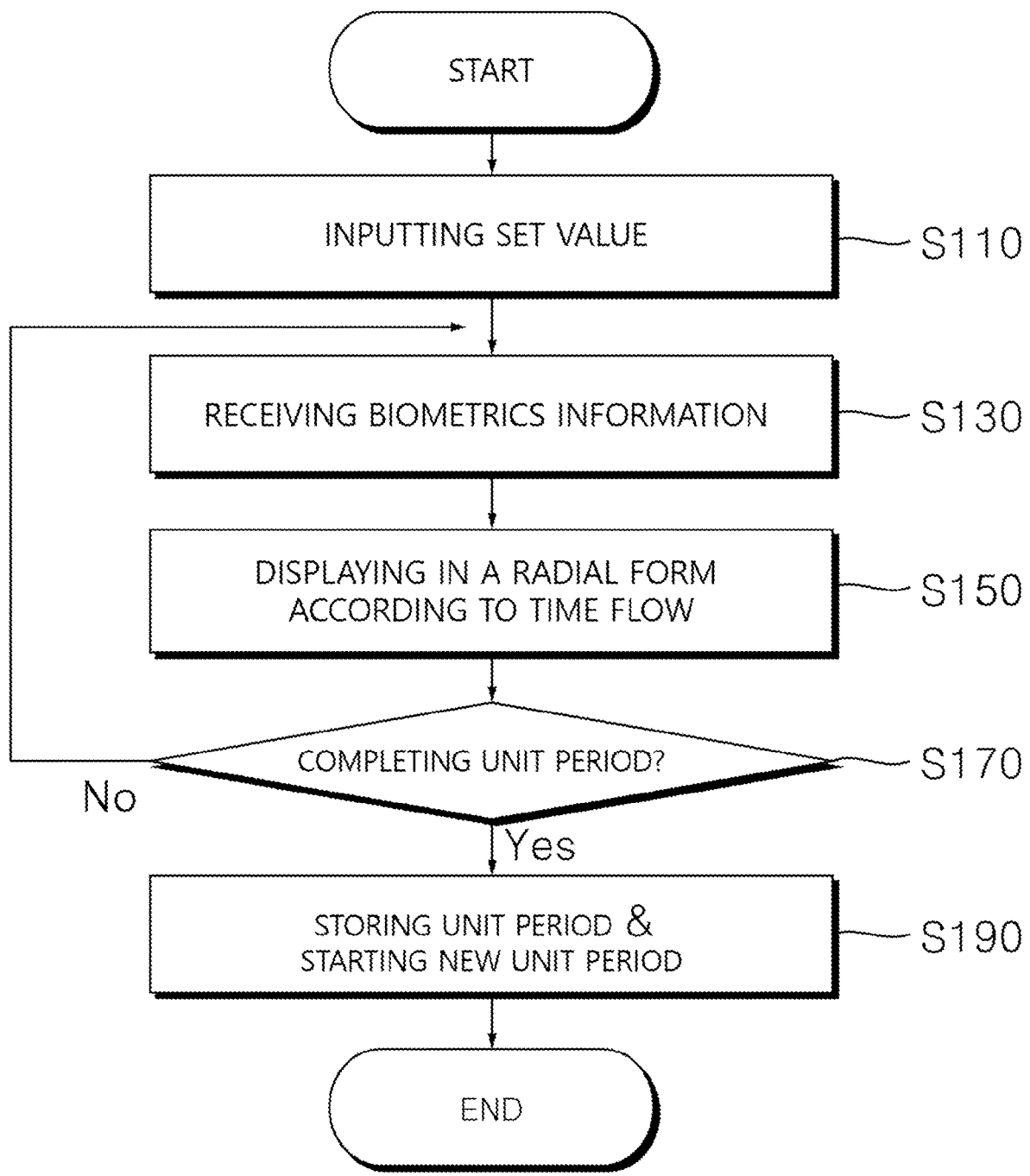
FIG. 4 is a flow chart for illustrating a method for outing blood glucose information according to an embodiment of the present disclosure.

FIG. 4 is a flow chart for illustrating a method for outing blood glucose information according to an embodiment of the present disclosure.

Referring to FIG. 4, when a user command for inputting a set value is inputted, the set value is set according to the inputted user command (S110). The set value may be a set value of an upper limit blood glucose or a set value of a lower limit blood glucose to easily detect hyperglycemia or hypoglycemia based on blood glucose information of a user depending on physical conditions of the user. Additionally, the set value may be a unit period set value for changeably setting a unit period to 12 hours, 1 day, 2 days, and so on or a set value for setting the maximum value and the minimum value of the displayed blood glucose level.

When the blood glucose information of the user is received from the continuous blood glucose measurement device for a unit period (S130), the blood glucose information of the user is mapped with a measurement time and a blood glucose level displayed on a display unit and is displayed, and latest measured blood glucose information among measurement times of the blood glucose information is located on a fixed reference line and previously measured blood glucose information is rotated in a clockwise or counterclockwise direction from the refence line according to time flow of the measurement times and is sequentially outputted and displayed (S150).

Whether the blood glucose information for the set unit period is received is determined (S170), and when the reception of the blood glucose information for the unit period is completed, the blood glucose information for the received unit period is registered and stored and blood glucose information received for new unit period is mapped with the measurement time and the blood glucose level displayed on the display unit is displayed (S190).

Figure 5:
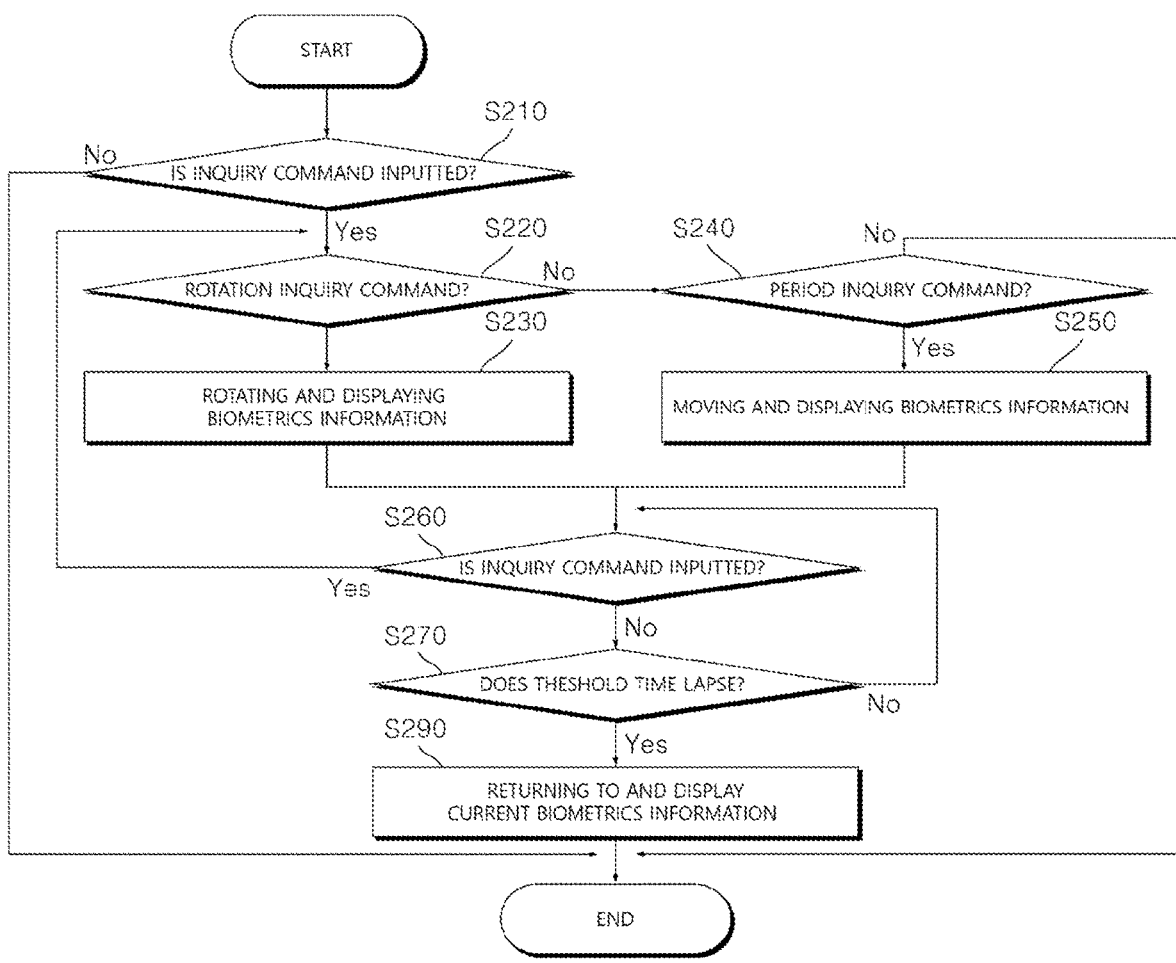
FIG. 5 is a flow chart for illustrating a method for displaying blood glucose information on a display unit according to an inquiry command of a user.

FIG. 5 is a flow chart for illustrating a method for displaying blood glucose information on a display unit according to an inquiry command of a user.

Referring to FIG. 5, whether a user command for inquiring blood glucose information is inputted is determined (S210). The latest measured blood glucose is located at a reference line and blood glucose information measured at previously measured times is rotated in a clockwise or counterclockwise direction from the reference line and is sequentially outputted according to time flow of the measurement times, and the blood glucose information of the measurement time positioned on the reference line is specifically displayed as an Arabic numeral at one portion of the display unit. The user can input a user commend for inquiring precise blood glucose information of previously measured time by moving blood glucose information measured at the previously measured time to the reference line, or input a user commend for inquiring blood glucose information of a previous unit period. Preferably, the display unit may be a touch screen and the user can touch the display unit or performs touch movement to input the user command.

By determining whether the inputted user command is a user command for rotating in a clockwise or counterclockwise direction the previously measured time to the reference line (220), when the user command is a rotation inquiry command, the displayed blood glucose is rotatedly moved in a clockwise or counterclockwise direction and displayed (S230).

Meanwhile, by determining whether the inputted user command is a user command for inquiring blood glucose information measured at a previous unit period or a following unit period by moving to the previous unit period (S240), when the user command is a movement inquiry command, the blood glucose information of the previous unit period or the following unit period is displayed by being sequentially moved to the previous unit period or the following unit period (S250).

By determining whether a different inquiry command is inputted within a preset threshold time from a rotation inquiry command or a movement inquiry command (S260), if the rotation inquiry command or the movement inquiry command is inputted within the preset threshold time, the blood glucose information of the previously measured time is displayed or the blood glucose information of the previous unit period or the following unit period is displayed according to the rotation inquiry command or the movement inquiry command.

However, if it is determined that the different inquiry command is not inputted within the preset threshold time (S270), the blood glucose information is displayed such that the most recently measured blood glucose information is located and returned to the reference line (S290).

Figure 6:
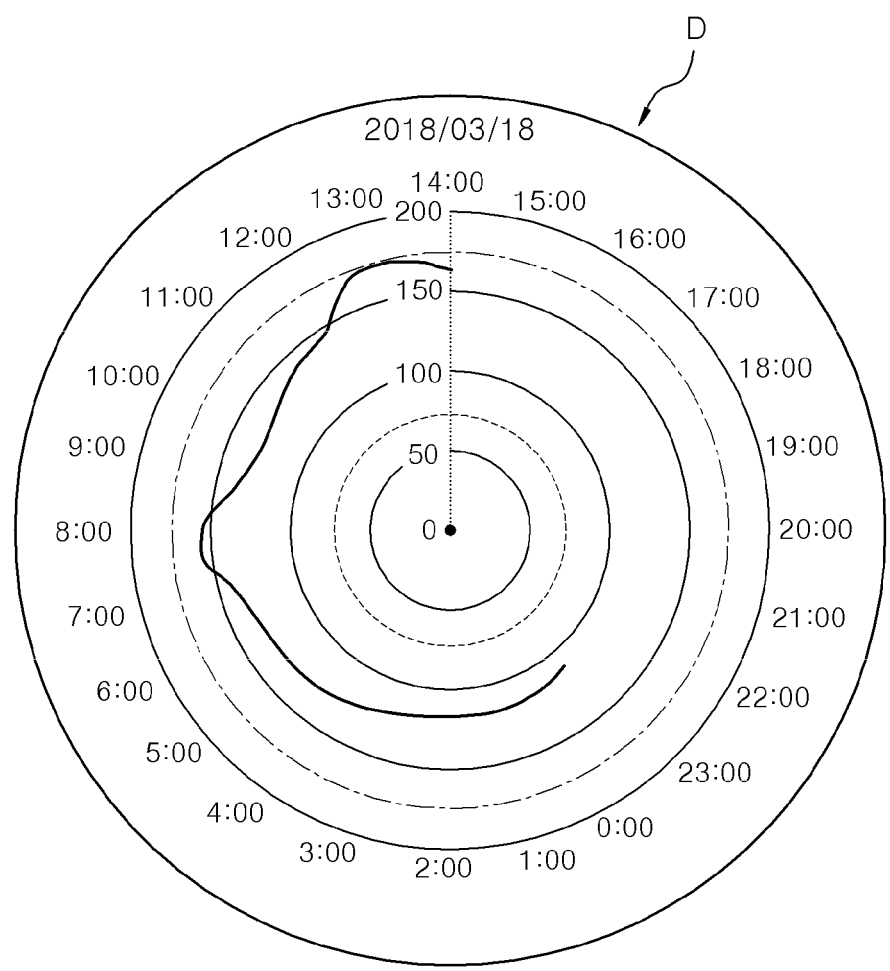
FIGS. 6 and 7 illustrate exemplary embodiments of biometric information displayed depending on a shape of a display unit according to a method for displaying blood glucose information according to an embodiment of the present disclosure.
Figure 7:
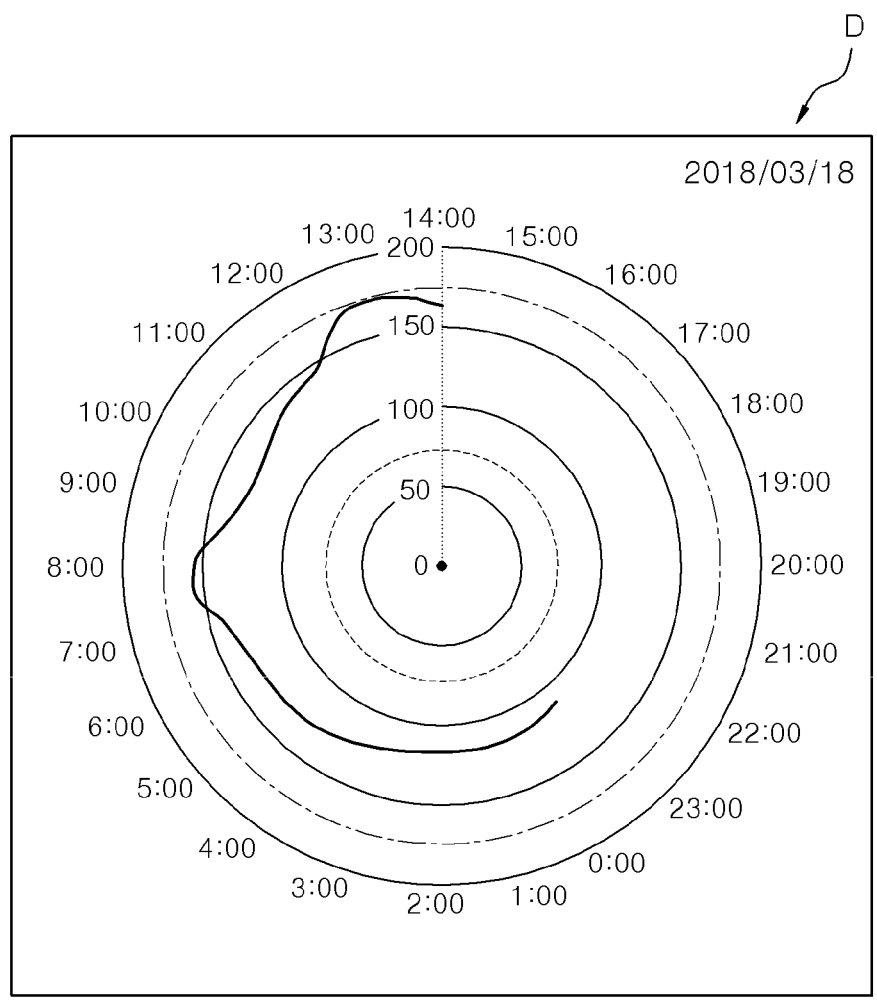

FIGS. 6 and 7 illustrate exemplary embodiments of biometric information displayed depending on a shape of a display unit according to a method for displaying blood glucose information according to an embodiment of the present disclosure.

As illustrated in FIG. 6, when a display unit (D) has a circular shape, on the display unit, measurement times of a unit period are separately disposed at a separation distance and displayed in a radial form in association with blood glucose levels having a shape of circle, and the blood glucose value and the measured time of the measured blood glucose information are mapped to the blood glucose levels and the measurement time of the unit period displayed on the display unit by being sequentially rotatedly moved in a counterclockwise and displayed. And, as illustrated in FIG. 7, when a display unit (D) has a square shape, on the display unit, measurement times of a unit period are separately disposed at a separation distance and displayed in a radial form in association with blood glucose levels having a shape of circle, and the blood glucose value and the measured time of the measured blood glucose information are mapped to the blood glucose levels and the measurement time of the unit period displayed on the display unit by being sequentially rotatedly moved in a counterclockwise and displayed.

Figure 8:
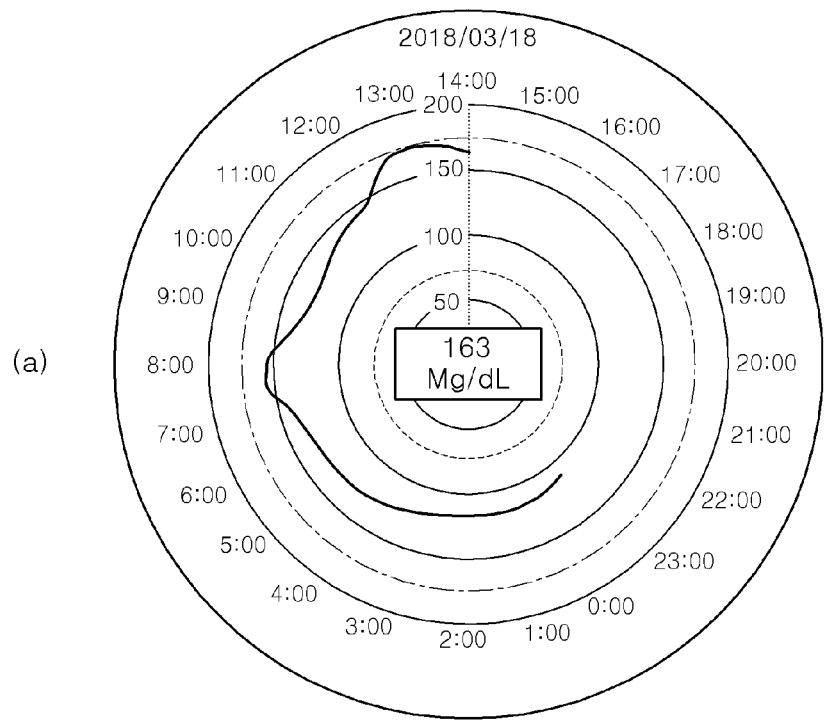
FIG. 8 is a drawing for illustrating an exemplary embodiment of blood glucose information displayed by a method for displaying blood glucose information according to an embodiment of the present disclosure.
Figure 8:
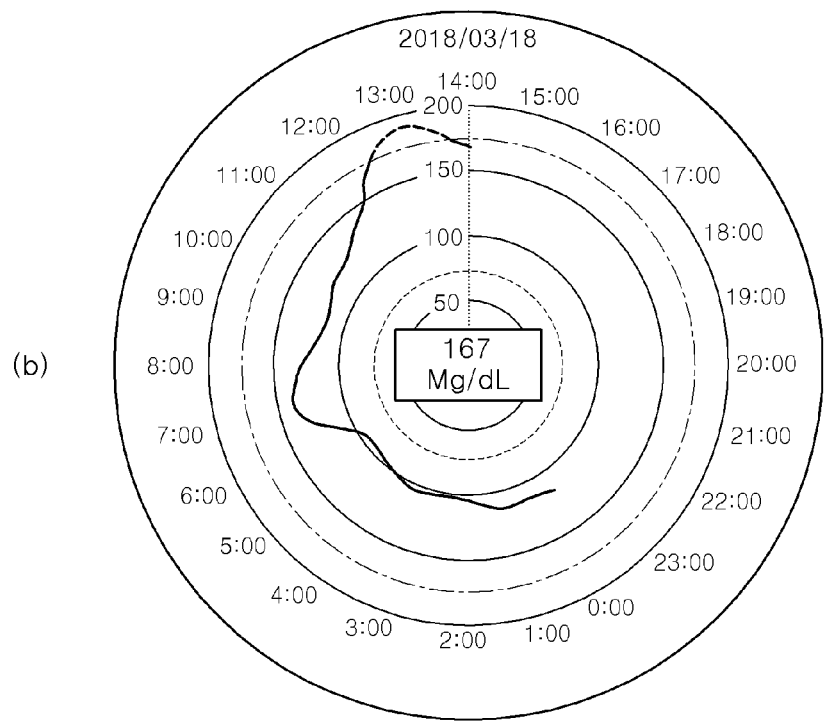

FIG. 8 is a drawing for illustrating an exemplary embodiment of blood glucose information displayed by a method for displaying blood glucose information according to an embodiment of the present disclosure.

As shown in FIG. 8(a), a reference blood glucose level (0 mg/DL) is displayed as a center of a circle and circles representing blood glucose levels which sequentially increase at a rate of 50 mg/dL are displayed in a radial form, and measurement times of a unit period are displayed around the outermost circle. For example, in case that the unit period of the blood glucose information displayed on a single display screen is a day, time is displayed at intervals of one hour.

When receiving the blood glucose information of the user, the blood glucose information of the user is displayed by being mapped to unit period measurement times and blood glucose levels, and the most recently measured blood glucose information among measurement times of the blood glucose information is located at a fixed reference line so that the blood glucose information measured at the previously measured times is sequentially outputted and displayed according to time flow of the measurement times by rotating the blood glucose information measured at the previously measured times in a counterclockwise direction from the reference line.

The latest measured blood glucose information is displayed at one portion of the display unit and, preferably, the latest measured blood glucose information is displayed with an Arabic numeral at a center of a circle of the blood glucose level.

Figure 9:
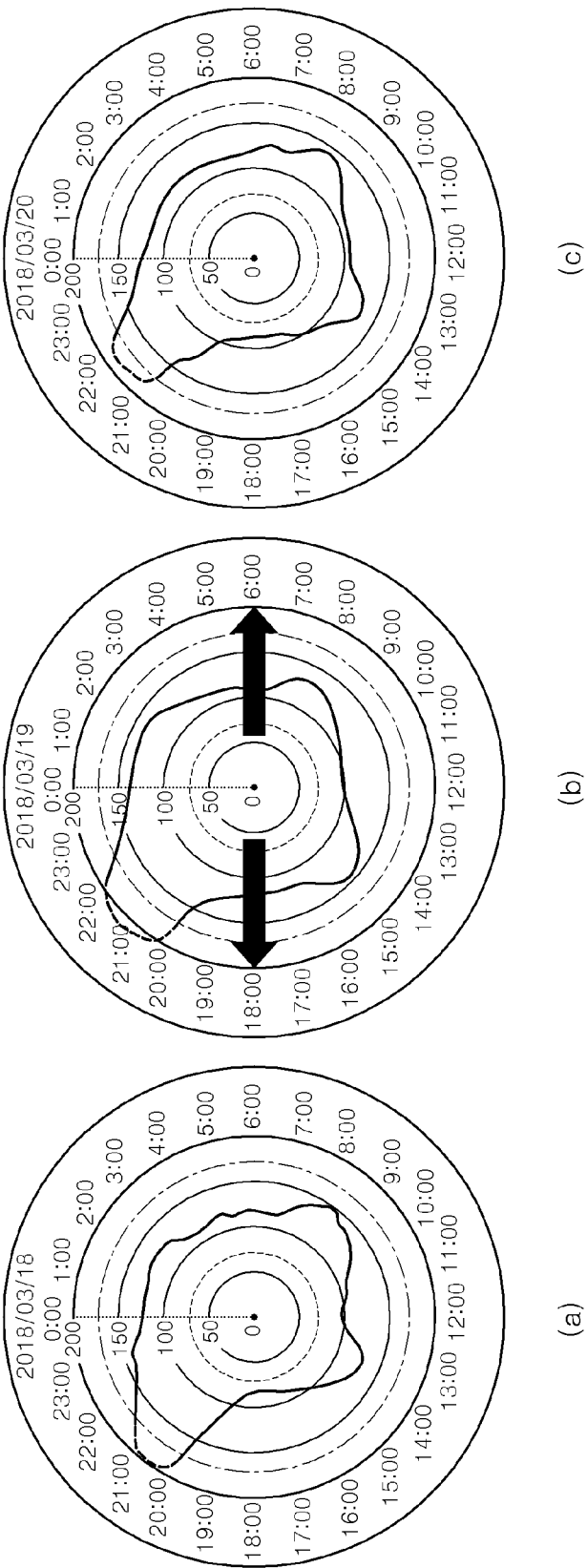
FIG. 9 is a drawing for illustrating an exemplary embodiment displaying blood glucose information according to a movement inquiry command.

Meanwhile, as illustrated in FIG. 8(b), when receiving blood glucose information of a user, the blood glucose information of the user is displayed by being mapped to unit period measurement times and blood glucose levels, and the latest measured blood glucose information among measurement times of the blood glucose information is located at a fixed reference line so that the blood glucose information measured at the previously measured times is sequentially outputted and displayed according to time flow of the measurement times by rotating the blood glucose information measured at the previously measured times in a counterclockwise direction from the reference line. In this embodiment, if there is a blood glucose value exceeding an upper limit blood glucose set value among the measured blood glucose information, that blood glucose information exceeding the upper limit blood glucose set value is distinguishably displayed in a different way from blood glucose information which is within between the upper limit blood glucose set value and the lower limit blood glucose set value so that the user can easily recognize blood glucose information, which is greater than the upper limit blood glucose set value or less than the lower limit blood glucose set value, among the blood glucose information of the unit period. Preferably, when a blood glucose value among the measured blood glucose information exceeds an upper limit blood glucose set value, that blood glucose information exceeding the upper limit blood glucose set value is displayed with a different color from blood glucose information which is within between the upper limit blood glucose set value and the lower limit blood glucose set value FIG. 9 is a drawing for illustrating an exemplary embodiment displaying blood glucose information according to a movement inquiry command.

As illustrated in FIG. 9(b), for example, when in a state that blood glucose information of a unit period of Mar. 19, 2018 is displayed on a display unit a movement inquiry command for inquiring blood glucose information of a previous unit period (e.g. Mar. 18, 2018) is inputted, the blood glucose information of the previous unit period is displayed on the display unit according to the inputted movement inquiry command as illustrated in FIG. 9(a).

Meanwhile, when in a state that blood glucose information of a unit period of Mar. 19, 2018 is displayed on the display unit a movement inquiry command for inquiring blood glucose information of a following unit period (e.g. Mar. 20, 2018) is inputted, the blood glucose information of the following unit period is displayed on the display unit according to the inputted movement inquiry command as illustrated in FIG. 9(c).

In the exemplary embodiment, the display unit is a touch screen, and the movement inquiry command can be inputted by scrolling the touch screen in a left direction or scrolling the touch screen in a right direction to input the previous inquiry command or the next inquiry command.

Therefore, an exemplary embodiment of the present disclosure displays biometrics information on a single display screen by sequentially rotating biometrics information by unit period according to measurement times so that the biometrics information by unit period can be easily inquired according to the movement inquiry command.

Figure 10:
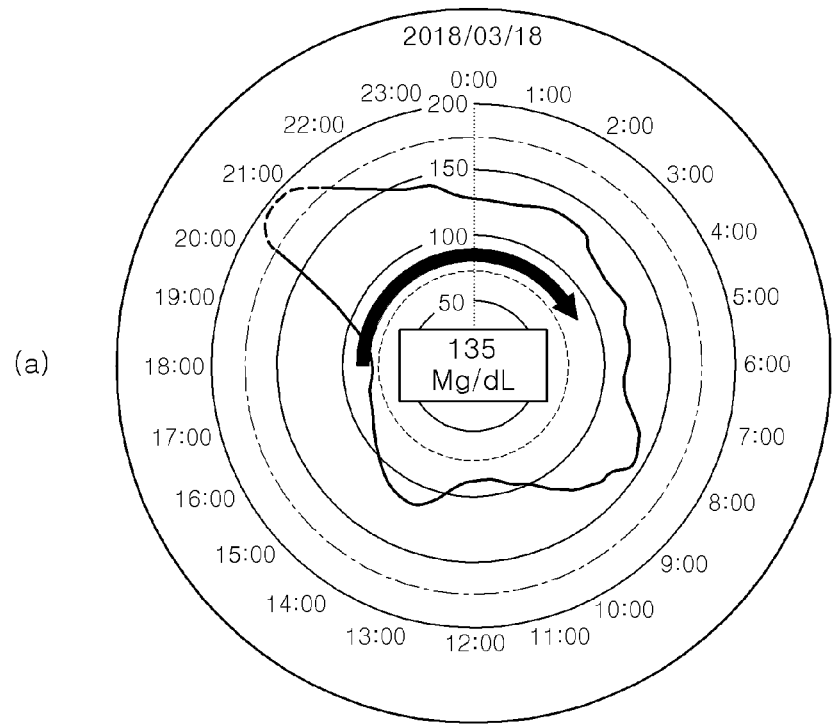
FIG. 10 is a drawing for illustrating an exemplary embodiment displaying biometrics information according to a rotation inquiry command.
Figure 10:
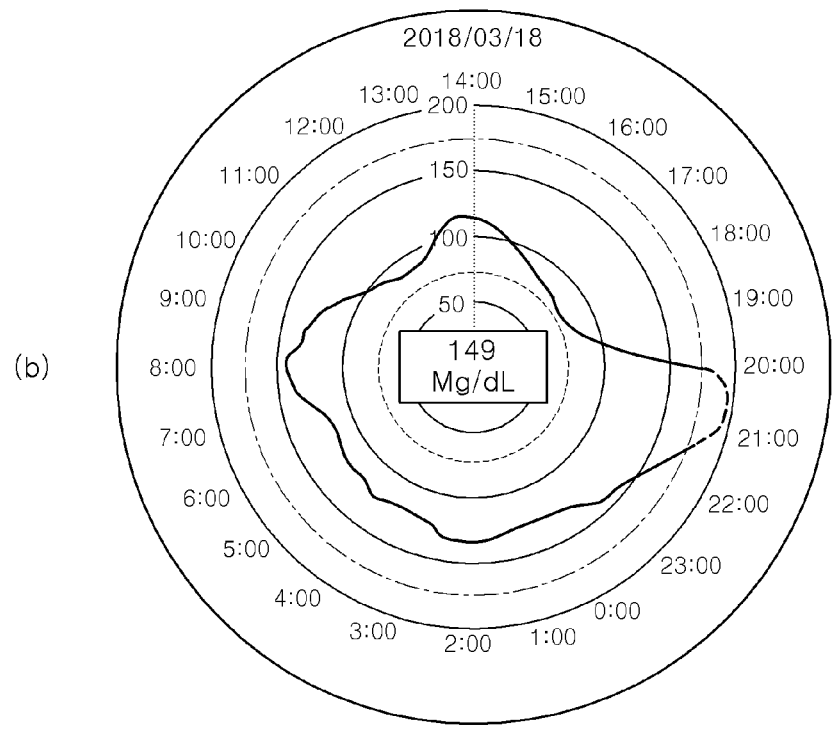

FIG. 10 is a drawing for illustrating an exemplary embodiment displaying biometrics information according to a rotation inquiry command.

As illustrated in FIG. 10(a), for example, when in a state that blood glucose information of a unit period of Mar. 18, 2018 is displayed on a display unit and measurement time 00:00 is positioned at a reference line a rotation inquiry command for inquiring blood glucose information of measurement time 14:00 is inputted, the blood glucose information of measurement time 14:00 is located at the reference line and the blood glucose information of measurement time 14:00 is displayed with an Arabic numeral according to the inputted rotation inquiry command as shown in FIG. 10(b).

Meanwhile, the exemplary embodiments of the present disclosure described above can be implemented through programs executable at computers, and can be operated in a general-purpose digital computer executing the programs using computer readable medium.

The above-referenced computer readable medium comprises storage medium such as magnetic storage media (e.g., ROM, floppy disks, hard disks, etc.), optical recording media (e.g., CD-ROMs, DVDs, etc.), and carrier waves (e.g., transmission through the Internet).

Although the present disclosure is described with reference to embodiments shown in the drawings in order to explain certain principles of the present disclosure by way of example, a person having ordinary skill in the art which the present disclosure relates could make various modifications and equivalent other embodiments. Accordingly, the protection scope of the present disclosure shall be defined by the claims attached hereto and all of their equivalents.

What is claimed is:

1. A method for displaying biometrics information, the method comprising:
   receiving biometrics information of a user; and
   sequentially displaying the received biometrics information on a display unit by rotating the received biometrics information around a reference level according to time flow of measurement times of measuring the biometrics information;
   determining whether biometrics information measured for a unit period is received;
   if the biometrics information measured for the unit period is received, mapping the received biometrics information to the unit period and registering and storing the received biometrics information mapped to the unit period;
   rotating biometrics information received for a new unit period around the reference level according to the time flow of the measurement times of the biometrics information and sequentially display the biometrics information;
   receiving a user command for selecting the biometrics information of the unit period by moving in a left direction or a right direction; and
   displaying the biometrics information of the unit period which the user inquires to monitor by moving in the left direction for display biometrics information measured at a previous unit period relative to current unit period or by moving in the right direction for display biometrics information measured at a following unit period relative to current unit period according to the received user command,
   wherein the user command is a user command for inquiring biometrics information measured at a previous unit period relative to current unit period or a following unit period relative to current unit period by moving to the previous unit period or the following unit period.

2. The method for displaying the biometrics information according to claim 1, wherein the method for displaying the biometrics information locates latest measured biometrics information among the measurement times of measuring the biometrics information at a reference line, and sequentially displays previously measured biometric information by rotating the previously measured biometric information in a clockwise or counterclockwise direction from the reference line according to the time flow of the measurement times.

3. The method for displaying the biometrics information according to claim 2, further comprising:
   receiving a first user command for selecting measurement time which the user inquires to monitor among the biometric information received and rotated in the clockwise or counterclockwise direction; and
   rotately moving and displaying the received biometric information with reference to the reference line which is set by the measurement time, which the user inquires to monitor, selected according to the received first user command.

4. The method for displaying the biometrics information according to claim 3, wherein the reference line is fixed and the received biometrics information is rotately moved with reference to the reference line which is the measurement time selected according to the first user command.

5. The method for displaying the biometrics information according to claim 4, wherein, when the first user command is not inputted within a preset threshold time, the latest measured biometrics information among the measurement times of measuring the biometrics information is located at the reference line and the previously measured biometric information is sequentially displayed by rotating the previously measured biometric information in the clockwise or counterclockwise direction from the reference line according to the time flow of the measurement times.

6. The method for displaying the biometrics information according to claim 3, wherein the biometrics information measured at a measurement time located at the reference line is displayed with an Arabic numeral at one portion of the display unit.

7. The method for displaying the biometrics information according to claim 6, wherein the biometrics information measured at a measurement time located at the reference line is displayed with an Arabic numeral at a center of rotation.

8. The method for displaying the biometrics information according to claim 2, further comprising:
receiving a second user information for setting a set value; and
display the set value in a circular shape.

9. The method for displaying the biometrics information according to claim 8, wherein biometrics information which is out of the set value among the received biometrics information is displayed with a different color from biometrics information which is within the set value.

10. The method for displaying the biometrics information according to claim 1, wherein, when the third user command is not inputted for a preset threshold time, biometrics information of a current unit period is displayed on the display unit.

* * * * *